US012390488B2

(12) United States Patent
Cohen et al.

(10) Patent No.: US 12,390,488 B2
(45) Date of Patent: Aug. 19, 2025

(54) ORAL ARTICLES AND METHODS OF USE

(71) Applicant: Solventum Intellectual Properties Company, Maplewood, MN (US)

(72) Inventors: Hannah C. Cohen, St. Paul, MN (US);
Katie F. Wlaschin, St. Paul, MN (US);
Yizhong Wang, Woodbury, MN (US);
Amanda C. Engler, Woodbury, MN (US); Jie Yang, Woodbury, MN (US);
Tiffany T. Ton, Woodbury, MN (US);
Joel D. Oxman, Minneapolis, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 296 days.

(21) Appl. No.: 17/419,527

(22) PCT Filed: Dec. 27, 2019

(86) PCT No.: PCT/IB2019/061406
§ 371 (c)(1),
(2) Date: Jun. 29, 2021

(87) PCT Pub. No.: WO2020/136620
PCT Pub. Date: Jul. 2, 2020

(65) Prior Publication Data
US 2022/0079976 A1 Mar. 17, 2022

Related U.S. Application Data

(60) Provisional application No. 62/786,359, filed on Dec. 29, 2018.

(51) Int. Cl.
| | |
|---|---|
| *A61K 8/06* | (2006.01) |
| *A61K 8/25* | (2006.01) |
| *A61K 8/92* | (2006.01) |
| *A61K 9/20* | (2006.01) |
| *A61K 33/00* | (2006.01) |
| *A61Q 11/00* | (2006.01) |

(52) U.S. Cl.
CPC ................ *A61K 33/00* (2013.01); *A61K 8/25* (2013.01); *A61K 8/922* (2013.01)

(58) Field of Classification Search
CPC ........ A61K 9/0053; A61K 47/44; A61K 9/20; A61K 9/2013; A61K 2800/92; A61K 8/92; A61K 9/006; A61K 8/0216; A61K 9/00; A61K 9/48; A61K 8/25; A61K 9/0056; A61K 8/922; A61K 8/064; A61K 9/107; A61K 9/10; A61K 8/06; A61Q 11/00

See application file for complete search history.

(56) References Cited

U.S. PATENT DOCUMENTS

| | | |
|---|---|---|
| 4,906,455 A | 3/1990 | Hoerman |
| 4,971,788 A | 11/1990 | Tabibi |
| 5,130,122 A | 7/1992 | Tabibi |
| 5,332,595 A | 7/1994 | Gaonkar |
| 5,401,496 A | 3/1995 | Fitzig |
| 5,482,722 A | 1/1996 | Cook |
| 5,496,558 A | 3/1996 | Napolitano |
| 5,523,098 A | 6/1996 | Synosky |
| 5,614,207 A | 3/1997 | Shah |
| 5,618,522 A | 4/1997 | Kaleta |
| 5,711,936 A | 1/1998 | Hill |
| 5,733,529 A | 3/1998 | Hill |
| 6,060,078 A | 5/2000 | Lee |
| 6,159,459 A | 12/2000 | Hunter |
| 6,183,775 B1 | 2/2001 | Ventouras |
| 6,596,298 B2 | 7/2003 | Leung |
| 6,682,756 B1 | 1/2004 | Horstmann |
| 7,025,983 B2 | 4/2006 | Leung |
| 7,407,669 B2 | 8/2008 | Leung |
| 7,648,712 B2 | 1/2010 | Bess |
| 7,867,509 B2 | 1/2011 | Leung |
| 8,197,851 B2 | 6/2012 | Bos |
| 8,367,650 B2 | 2/2013 | Desjonqueres |
| 8,460,689 B2 | 6/2013 | Wlaschin |
| 8,540,970 B2 | 9/2013 | Rodriguez-Vilaboa |
| 8,647,608 B2 | 2/2014 | Yang |
| 8,758,803 B2 | 6/2014 | Müller |
| 8,968,709 B2 | 3/2015 | Yang |
| 9,289,369 B2 | 3/2016 | Boyd |
| 9,320,690 B2 | 4/2016 | Ontumi |
| 9,539,205 B2 | 1/2017 | Haug |
| 9,724,278 B2 | 8/2017 | Lambert |
| 9,730,865 B2 | 8/2017 | Sullivan |
| 9,968,547 B2 | 5/2018 | Okay |

(Continued)

FOREIGN PATENT DOCUMENTS

| | | |
|---|---|---|
| AU | 2012205140 | 8/2012 |
| CN | 106666055 | 5/2017 |

(Continued)

OTHER PUBLICATIONS

The American Academy of Oral Medicine. Dry Mouth. May 16, 2016. <www.aaom.com/dry-mouth>. (Year: 2016).*
Arya, "Fast Dissolving Oral Films: An Innovative Drug Delivery System and Dosage Form", International Journal of ChemTech Research, Jan.-Mar. 2010, vol. 2, No. 1, pp. 576-583.
Dixit, "Oral strip technology: Overview and future potential", Journal of Controlled Release, 2009, vol. 139, No. 2, pp. 94-107.
Donaldson, "Xerostomia Treatment: A Systematic Approach to Xerostomia diagnosis and Management", Compendium eBook Continuing Education, Nov.-Dec. 2018, vol. 39, No. 20, 12 pages.

(Continued)

*Primary Examiner* — Tracy Liu

(57) ABSTRACT

Articles that include from 70 wt-% to 99 wt-% of one or more plant based oil that is solid at 25° C., the weight percent based on the total weight of the article; and from 0.5 wt-% to 10 wt-% of fumed silica, the weight percent based on the total weight of the article. Methods of use of the articles are also included.

19 Claims, 1 Drawing Sheet

(56) References Cited

U.S. PATENT DOCUMENTS

| | | | |
|---|---|---|---|
| 10,413,503 B2 | 9/2019 | Okay | |
| 10,744,082 B2 | 8/2020 | Okay | |
| 2003/0118628 A1 | 6/2003 | Tutuncu | |
| 2004/0141927 A1 | 7/2004 | Johnson | |
| 2004/0156794 A1 | 8/2004 | Barkalow | |
| 2005/0058744 A1* | 3/2005 | Steinberg | A23G 4/14 426/3 |
| 2005/0152972 A1 | 7/2005 | Singh | |
| 2005/0281772 A1 | 12/2005 | Bromley | |
| 2006/0188612 A1* | 8/2006 | Lorenzi | A23L 29/269 426/103 |
| 2006/0204559 A1 | 9/2006 | Bess | |
| 2006/0263412 A1* | 11/2006 | Pan | A61K 36/55 424/440 |
| 2007/0031561 A1 | 2/2007 | Lakkis | |
| 2007/0154411 A1 | 7/2007 | Barth | |
| 2007/0183985 A1 | 8/2007 | Tallia | |
| 2007/0190090 A1 | 8/2007 | Brown | |
| 2008/0020024 A1 | 1/2008 | Kulkarni | |
| 2008/0241080 A1 | 10/2008 | Rodriguez-Vilaboa | |
| 2009/0081291 A1 | 3/2009 | Gin | |
| 2009/0081294 A1 | 3/2009 | Gin | |
| 2009/0297570 A1* | 12/2009 | Groves | A61Q 11/00 264/4.4 |
| 2009/0311200 A1 | 12/2009 | Lambert | |
| 2010/0062988 A1* | 3/2010 | Chen | A61K 9/2063 514/23 |
| 2010/0098791 A1 | 4/2010 | Rodriguez-Vilaboa | |
| 2010/0233221 A1 | 9/2010 | Folmer | |
| 2010/0247644 A1 | 9/2010 | Domb | |
| 2011/0027328 A1 | 2/2011 | Baig | |
| 2011/0104081 A1 | 5/2011 | Scott | |
| 2011/0171342 A1 | 7/2011 | Phillips, III | |
| 2012/0058158 A1 | 3/2012 | Booles | |
| 2013/0052146 A1 | 2/2013 | Yang | |
| 2013/0269133 A1 | 10/2013 | Ontumi | |
| 2013/0309291 A1 | 11/2013 | Stoll | |
| 2014/0154394 A1* | 6/2014 | Arfsten | A23D 9/007 426/609 |
| 2014/0155457 A1 | 6/2014 | Nho | |
| 2015/0056325 A1* | 2/2015 | Kabse | A23G 3/34 426/5 |
| 2015/0216887 A1 | 8/2015 | Derrieu | |
| 2015/0290107 A1 | 10/2015 | Okay | |
| 2019/0083220 A1 | 3/2019 | Wlaschin | |
| 2021/0161800 A1 | 6/2021 | Okay | |

FOREIGN PATENT DOCUMENTS

| | | | |
|---|---|---|---|
| EP | 1674078 | | 6/2006 |
| EP | 1676557 | | 7/2006 |
| EP | 2027852 | | 2/2009 |
| EP | 3315117 A1 * | 5/2018 | A61K 8/064 |
| GB | 2139919 | | 11/1984 |
| GB | 2242358 | | 4/1994 |
| WO | WO 1996-039116 | | 12/1996 |
| WO | WO 1999-029686 | | 6/1999 |
| WO | WO 2002-022096 | | 3/2002 |
| WO | WO 2004-096192 | | 11/2004 |
| WO | WO 2009-014907 | | 1/2009 |
| WO | WO 2009-042968 | | 4/2009 |
| WO | WO 2012-087279 | | 6/2012 |
| WO | WO 2012-087280 | | 6/2012 |
| WO | WO 2012-087281 | | 6/2012 |
| WO | WO 2014-053263 | | 4/2014 |
| WO | WO 2014-098868 | | 6/2014 |
| WO | WO 2014-166994 | | 10/2014 |
| WO | WO 2016-207299 | | 12/2016 |
| WO | WO 2017-042275 | | 3/2017 |
| WO | WO 2017-205230 | | 11/2017 |
| WO | WO 2017-218421 | | 12/2017 |
| WO | WO 2018-029671 | | 2/2018 |
| WO | WO 2019-123171 | | 6/2019 |
| WO | WO 2019-123261 | | 6/2019 |
| WO | WO 2020-136604 | | 7/2020 |
| WO | WO 2020-136606 | | 7/2020 |

OTHER PUBLICATIONS

Donaldson, "Xerostomia Update: Comprehensive and Systematic Diagnosis and Management", Jan. 2020, CDE World eBook, Continuing Dental Education, Dental Learning Systems, LLC, vol. 7, No. 158, 16 pages.

"Dry Mouth—Seniors Oral Health", Washington Dental Service Foundation [on line], 2017, [retrieved from the internet on Apr. 6, 2022], URL <http://seniorsoralhealth.org/dry-mouth/?doing_wp_cron=1471029828.7616550922393798828125>, 2 pages.

"Frozen Reverse Spherification—Molecular Recipes", KQ2 Ventures LLC [on line], Mar. 2014, [retrieved from the internet on Apr. 4, 2022], URL <http://www.molecularrecipes.com/spherification-class/frozen-reverse-spherification/>, 5 pages.

Furness, "Interventions for the Management of Dry Mouth: Topical Therapies (Review)", Cochrane database of systematic reviews, 2011, vol. 12, No. 12, pp. 1-93.

Horne, "What Causes Dry Mouth", MedicineNet [on line], Mar. 2020, [retrieved from the internet on Apr. 4, 2022], URL <https://www.medicinenet.com/dry_mouth/article.htm>, 8 pages.

Kelly, "Bioadhesive, rheological, lubricant and other aspects of an oral gel formulation intended for the treatment of xerostomia", International Journal of Pharmaceutics, 2004, vol. 278, pp. 391-406.

Patel, "Effect of subgingival application of topical ozonated olive oil in the treatment of chronic periodontitis: a randomized, controlled, double blind, clinical and microbiological study". Minerva Stomatol, 2012. vol. 61 No. 9 pp. 381-398.

Patel, "Therapeutic effect of topical ozonated oil on the epithelial healing of palatal wound sites: a planimetrical and cytological study". Journal of Investigative and Clinical Detistry, Jul. 2011, vol. 2, No. 4, pp. 248-258.

"Reverse Spherification—Molecular Recipes", KQ2 Ventures LLC [on line], Mar. 2014, [retrieved from the internet on Apr. 4, 2022], URL <http://www.molecularrecipes.com/spherification-class/reverse-spherification/>, 10 pages.

Russo, "A focus on mucoadhesive polymers and their application in buccal dosage forms", Journal of Drug Delivery Science and Technology, 2016, vol. 32, pp. 113-125.

Saha, "Hydrocolloids as thickening and gelling agents in food: a critical review", Journal of Food Science and Technology, Nov.-Dec. 2010, vol. 47 No. 6 pp. 587-597.

Video: "Encapsulation of Oil Isomalt Technical Sugar" Oct. 2013 URL <https://www.youtube.com/watch?v=4t8BzzaX-iY6>, 00:01:24 HRS.

Zhang, "Food-grade filled hydrogels for oral delivery of lipophilic active ingredients: Temperature-triggered release microgels", Food Research International, 2015, vol. 69, pp. 274-280.

International Search Report for PCT International Application No. PCT-IB2019-061378, mailed on Jun. 23, 2020, 6 pages.

International Search Report for PCT International Application No. PCT-IB2019-061380, mailed on Apr. 29, 2020, 6 pages.

International Search Report for PCT International Application No. PCT-IB2019-061406, mailed on Apr. 14, 2020, 4 pages.

* cited by examiner

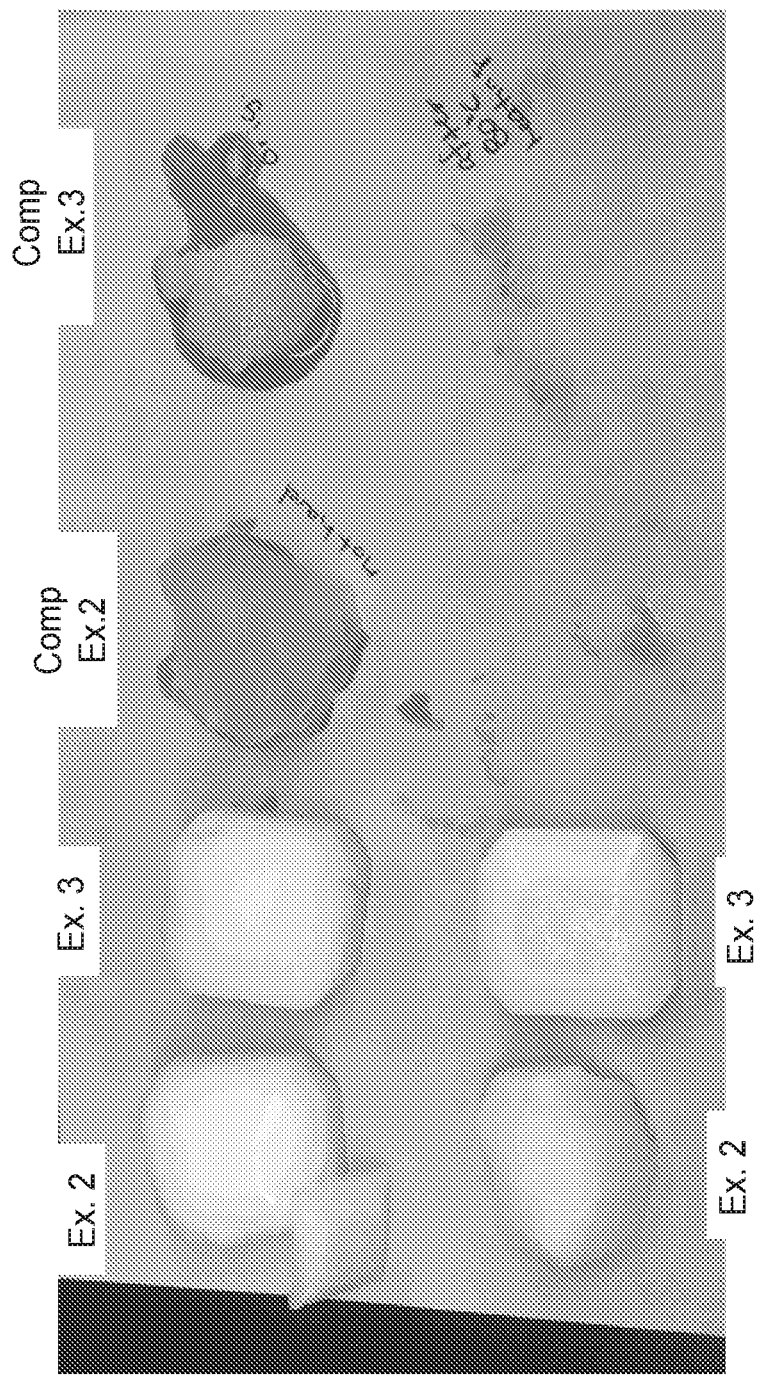

ORAL ARTICLES AND METHODS OF USE

CROSS REFERENCE TO RELATED APPLICATIONS

This application is a national stage filing under 35 U.S.C. 371 of PCT/IB2019/061406, filed 27 Dec. 2019, which claims the benefit of U.S. Provisional Application No. 62/786,359, filed 29 Dec. 2018, the disclosures of each of which are incorporated by reference herein in their entireties.

SUMMARY

Disclosed herein are articles that include from 70 wt-% to 99 wt-% of one or more plant based oil that is solid at room temperature (25° C.), the weight percent based on the total weight of the article; and from 0.5 wt-% to 10 wt-% of fumed silica, the weight percent based on the total weight of the article, wherein the article is solid set and homogeneous.

Also disclosed are methods of preventing, inhibiting, disrupting, or any combination thereof the formation or maintenance of a biofilm in an oral tissue, the methods including contacting an oral tissue with disclosed articles.

Also disclosed are methods of affecting hydration loss in an oral tissue, the methods including contacting an oral tissue with disclosed articles.

Also disclosed are methods of affecting lubricity or lubriciousness in an oral tissue, the methods including contacting an oral tissue with disclosed articles.

Also disclosed are methods of affecting the effects of xerostomia, dry mouth, or both, the methods including contacting an oral tissue with disclosed articles.

The above summary is not intended to describe each embodiment of the present disclosure. The details of one or more embodiments of the present disclosure are also set forth in the description below. Other features, objects, and advantages of the present disclosure will be apparent from the description and from the claims.

BRIEF DESCRIPTION OF DRAWINGS

The disclosure may be more completely understood in consideration of the following detailed description of various illustrative embodiments in connection with the accompanying drawings, in which:

FIG. 1 shows photographs of the lozenges prepared above. The top row shows Example 3 and Comparative Examples 1 and 2. The bottom row shows Examples 2 and 3 that were poured after re-heating the mixed solution to 80° C.

DETAILED DESCRIPTION

Xerostomia or dry mouth is a common condition that results from insufficient saliva volume. It is increasingly prevalent in the aging population and is a side-effect of many medications, as well as cancer treatment. Severe cases of xerostomia are often related to salivary gland dysfunction, known as Sjögren's Syndrome.

The lack of moisture and lubrication typically provided by saliva has a range of negative effects on oral tissue (soft tissue) ranging from mild discomfort to extremely painful and infected mouth sores. The persistent discomfort and dryness can also contribute to larger health issues by causing disruption of sleep, and impairing one's ability to talk (socialize, may impact psychological health) and eat (may impact nutrition). Dry buccal tissue is a less effective barrier and more susceptible to penetration by physical irritants such as toxins and carcinogens in foods, beverages and tobacco.

Saliva is also the mouth's primary defense against tooth decay. Healthy saliva flow helps prevent cavities by physically removing bacteria from the oral cavity before they can become attached to tooth and tissue surfaces and form a protected biofilm. The flow of saliva also helps dilute sugars and acids introduced by intake of food and beverages. The buffering capacity neutralizes acids and aids in the digestive process. The presence of calcium and phosphate salts provides continuous opportunity for re-mineralization of tooth enamel, serving to reverse the tooth decay process.

Many who suffer with xerostomia use separate products to address hard tissue health and soft tissue comfort. For soft tissue comfort, saliva substitute products are typically designed to provide lubrication and moisture. The format of these products is varied, and includes viscous gels/pastes, sprays, rinses, mints, and slow-release tablets. These are applied multiple-times per day or as needed for comfort. For hard-tissue health, different treatments are used to directly address cavity prevention (antiseptic rinses, fluoride products, calcium/phosphate treatments). Often "dry mouth-friendly" versions of products, such as toothpastes and mouth rinses are recommended. Dry mouth friendly products typically have a neutral pH and do not contain alcohol or other irritating components (e.g. anionic surfactants or emulsifiers).

There is a desire to design a single product that effectively and easily addresses the need for dry mouth symptom relief (soft tissue comfort) and oral health preventative benefits (tooth enamel and cavity protection). A fully ingestible, lozenge type product is well suited for this purpose. It addresses both the health of hard-tissue and soft tissue.

Disclosed herein are articles that can be utilized as oral articles, for example. Disclosed articles can be in the form of a lozenge, for example. Disclosed articles are not gums. A gum does not dissolve in the mouth of a user, whereas a lozenge does dissolve in the mouth of a user.

Disclosed articles, one or more components in an article, or both can be characterized as edible. Referring to a component, composition or article as edible can mean that the particular ingredient, composition or article is safe for daily, long-term ingestion at recommended use levels. In some embodiments, the GRAS (generally regarded as safe) list from the United States Food and Drug Administration (FDA) can be utilized to determine if a component is edible at the levels utilized in a composition.

Disclosed articles include one or more useful oil, and fumed silica.

Disclosed articles include one or more oil that is a solid at room temperature (25° C.). In some embodiments, useful oils do not include silicone based oils (e.g., simethicone or dimethicone). Useful oils can include any oils, but in some embodiments can include plant based oils. Many plant based oils can be made to exist as a solid at room temperature by hydrogenating them. The articles can include a single edible oil, or as many as two, three, four, five or more edible oils. Examples of suitable edible oils that are solid at room temperature can include, but are not limited to hydrogenated plant based oils and the like, and mixtures or fractions thereof. A specific and non-limiting example includes cocoa butter.

Disclosed articles can include not less than 70 percent of one or more oils that are solid at room temperature based on the total weight of the article, not less than 75 percent of one or more oils that are solid at room temperature based on the total weight of the article, not less than 76 percent of one or more oils that are solid at room temperature based on the total weight of the article, not less than 80 percent of one or more oils that are solid at room temperature based on the total weight of the article, or not less than 85 percent of one or more oils that are solid at room temperature based on the total weight of the article. Disclosed articles can include not greater than 99 percent of one or more oils that are solid at room temperature based on the total weight of the article, not greater than 97 percent of one or more oils that are solid at room temperature based on the total weight of the article, or not greater than 95 percent of one or more oils that are solid at room temperature based on the total weight of the article.

Disclosed articles also include fumed silica. In some embodiments, disclosed articles can include not less than 0.5 percent of fumed silica based on the total weight of the article, not less than 1 percent of fumed silica based on the total weight of the article, not less than 2 percent fumed silica based on the total weight of the article, or not less than 4 percent fumed silica based on the total weight of the article. In some embodiments, disclosed article can include not greater than 10 percent fumed silica based on the total weight of the article, not greater than 9 percent fumed silica based on the total weight of the article, or not greater than 8.5 percent of fumed silica based on the total weight of the article.

In some embodiments, disclosed articles can also optionally include water. The water can be used to contain water soluble materials within the final article. In some embodiments, water can be added to a composition to make a disclosed article in combination with a number of different components, for example as a buffer solution. Illustrative materials can include minerals (e.g., calcium), sweeteners, etc. In some embodiments, disclosed articles can include not less than 0.5 percent water based on the total weight of the article, not less than 1 percent water based on the total weight of the article, or not less than 2 percent water based on the total weight of the article. In some embodiments, disclosed articles can include not greater than 10 percent water based on the total weight of the article, not greater than 8 percent water based on the total weight of the article, or not greater than 5 percent water based on the total weight of the article.

Disclosed articles can also optionally include additional components other than those discussed above. Illustrative optional components can include, for example, sweeteners (e.g., non-carcinogenic sweeteners), mineral salts, buffering components, flavorants, preservative agents, humectants, or combinations thereof. Other optional beneficial ingredients can also be included at appropriate levels such as, aloe vera (multi-benefit), folic acid (related to B12), hyaluronic acid (lubricating, moisturizing), ceramides, amino acids (e.g., glycine, arginine), betaines or oxygenated glycerol triesters, vitamin E (antioxidant), vitamin B12 EDTA, cetyl pyridinium chloride, chlorhexidine, other antiseptics, etc., or combinations thereof.

In some embodiments, disclosed articles can include flavorants including for example, spearmint, peppermint, strawberry, butter, vanilla, coconut, almond, bubble gum, berry, fruit punch, butterscotch, caramel, or combinations thereof. In some embodiments, some flavorants, e.g., mint, citrus, etc. can also be advantageous because they stimulate salivary production when utilized in articles. Artificial sweeteners may also be used (stevia, aspartame, sucralose, neotame, acesulfame potassium (Ace-K), saccharin, and advantame, for example). In some embodiments, disclosed articles can include one or more sweeteners including for example, non-cariogenic polyols, or sugar substitutes (e.g., sucralose). In some embodiments, disclosed articles can include non-cariogenic polyol sweeteners such as xylitol, sorbitol, maltitol, erythritol, isomalt, or combinations thereof. In some embodiments, disclosed articles can include non-cariogenic polyol sweeteners such as xylitol, sorbitol, or combinations thereof. In articles that include optional sweeteners, the sweetener can be present in an amount that is not less than 2.5 percent based on the total weight of the article or not less than 1 percent based on the total weight of the article. In some embodiments, an optional sweetener can be present in an amount that is not greater than 30 percent based on the total weight of the article, not greater than 20 percent based on the total weight of the article, not greater than 15 percent based on the total weight of the article, not greater than 10 percent based on the total weight of the article, or not greater than 8 percent based on the total weight of the article.

In some embodiments, disclosed articles can optionally include one or more minerals that may be useful or beneficial for ingestion or oral health. Illustrative optional minerals that can be included in disclosed articles can include calcium (Ca), phosphorus (P), magnesium (Mg), fluorine (F), iron (Fe), strontium (Sr), zinc (Zn), potassium (K), or combinations thereof. In some embodiments, some minerals can be provided by including magnesium chloride ($MgCl_2$), calcium chloride ($CaCl_2$), strontium chloride, zinc chloride, zinc gluconate, potassium nitrate, potassium phosphate dibasic ($KH_2PO_4$), or combinations thereof. In some embodiments, where fluorine is included, it can be included as the fluoride ion (F—) in salt form ($MgF_2$, $CaF_2$, etc.), at a concentration that is not greater than 4 milligrams per liter (mg/L).

In some embodiments, disclosed articles can include one or more preservatives to render the article microbiologically stable, to increase the microbiological stability thereof, or some combination thereof. In some embodiments, useful preservatives include those that work at a neutral pH, do not detrimentally affect taste, are edible, are effective against a broad spectrum of pathogens, or combinations thereof. Specific illustrative useful preservatives can include GEOGARD® preservatives, which are commercially available from Lonza (Basel, Switzerland) and include salicyclic acid, benzyl alcohol, sodium benzoate, potassium sorbate, parabens, natural preservatives, polyglyceryl esters, monolaurin,1,2 octanediol, caprylic/capric triglycerides, DHA, aloe vera, potassium sorbate, cetyl pyridinium chloride (CPP), polyhexamethylene biguanide (PHMB), methylparaben, and chlorhexidine gluconate (CHG) for example.

Disclosed articles can generally be formed by heating the one or more oil that is a solid at room temperature (25° C.) to melting and then adding the fumed silica. Optional ingredients can be dissolved in water, e.g., with heating. The water-based composition can then be added to the oil-based composition and the mixture can then be further mixed.

Disclosed articles can have varied properties. In some embodiments, disclosed articles can be described by the pH thereof, the viscosity thereof, the stability thereof, various other properties, or combinations thereof.

In some embodiments, disclosed articles can have a pH that is acceptable for use in the mouth of a person, for example. In some embodiments, disclosed articles can have a pH from 4.5 to 9.5, for example. In some embodiments, the article can have a pH in a more neutral range from 5.0-8.5 or 5.5-8.5 for example, as dry mouth sufferers can have a higher sensitivity to pH. The article can naturally have such a pH or can be buffered to have a pH in a useful, e.g., a "neutral" range.

In some embodiments, disclosed articles can be described as solid set (e.g., the article does not flow at room temperature (25° C.)) and homogenous (e.g., the article has no visible separation). In some embodiments, disclosed articles can be described as solid set and homogenous even after speed mixing, re-heating, cooling, or any combinations thereof. Articles that are solid set and homogeneous even after any of re-heating, cooling, or any combination thereof may be advantageous due to extreme environmental conditions that they may be subjected to by a user (e.g., storage of the articles in automobiles, which could subject them to extreme temperatures).

Disclosed articles can be packaged in any of a number of commonly utilized fashions, including for example blister packages, bags, etc. The articles themselves can also be molded into virtually any size or shapes.

In some embodiments, disclosed articles can have desired effects when utilized. Such effects can include, for example the article's effect on biofilms, the article's effect on plaque buildup, the article's effect on water loss, the article's ability to maintain or provide lubricating properties, resist dilution or wash-off by saliva or water, or drinking and eating in general or combinations thereof.

In some embodiments, disclosed articles can prevent, inhibit, disrupt the formation or maintenance of a biofilm in an area contacted with the article. The area contacted can be in vivo or in vitro. In some embodiments, an article can prevent, inhibit, disrupt the formation or maintenance of a biofilm in a mouth of a user where the article was applied to the mouth, for example via placing the article into the mouth when compared to a mouth without the article applied thereto. In some embodiments, an article can prevent, inhibit, disrupt the formation or maintenance of a biofilm in a container in which a biofilm exists and the article was applied to the container via contact when compared to a container without the article contacted thereto. Preventing, inhibiting, disrupting, or some combination thereof the formation or maintenance of biofilms can be measured using a modified version of the MBEC assay (described in ASTM E2799), which measures disruption of strep mutans biofilms grown on special pegs in a microtiter plate. The biofilms growing on the pegs are treated by periodic submersion into test materials, followed by washing in saliva and water. The biofilm remaining on each peg following treatment is quantified by measuring the amount of fluorescently labeled bacteria that eluted from the pegs at the end of the treatment cycles (see example). In some embodiments, disclosed articles can affect the buildup of plaque in an area contacted by the article. The area contacted can be in vivo or in vitro. In some embodiments, an article can decrease plaque buildup on at least one tooth in a mouth of a user where the article was applied to the mouth, for example via contacting the article into the mouth when compared to a mouth without the article applied thereto. In some embodiments, an article can decrease plaque buildup in a container in which plaque can develop and the article was applied to the container via pouring, spraying, etc. when compared to a container without the article contacted thereto. Decreasing plaque buildup can be measured by a variety of methods in vivo including for example plaque scoring, dyeing of plaque, etc.

In some embodiments, disclosed articles can affect hydration loss in an area contacted by the articles. The area contacted can be in vivo or in vitro. In some embodiments, an article can decrease hydration loss in a mouth of a user where the article was applied to the mouth, for example via contacting the article into the mouth when compared to a mouth without the article applied thereto. In some embodiments, an article can decrease hydration loss from a tissue in which hydration can be lost and the article was applied to the tissue via contact when compared to a tissue without the article applied thereto.

In some embodiments, disclosed articles can affect lubricity or lubriciousness of an area contacted by the article. The area contacted can be in vivo or in vitro. In some embodiments, an article can maintain or increase lubricity in a mouth of a user where the article was applied to the mouth, for example via contacting the article into the mouth when compared to a mouth without the article applied thereto.

Also disclosed herein are methods of using disclosed articles. Disclosed methods can include contacting an oral cavity or oral tissue with a disclosed article. The step of contacting the oral cavity or oral tissue can be accomplished by applying the article in any way, for example by simply placing the article in the mouth. Disclosed methods can be useful for preventing, inhibiting, disrupting, or any combination thereof the formation or maintenance of a biofilm in an area contacted with the article; for affecting hydration loss in an area contacted by the article; for affecting lubricity or lubriciousness of an area contacted by the article; for affecting or alleviating the effects of xerostomia, dry mouth, or both.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a composition that "comprises" silver may be a composition that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects is present. For example, a "second" substrate is merely intended to differentiate from another substrate (such as a "first" substrate). Use of "first," "second," etc. in the description above and the claims that follow is also not necessarily intended to indicate that one comes earlier in time than the other.

Example articles and techniques according to the disclosure provide will be illustrated by the following non-limiting examples.

EXAMPLES

TABLE 1

| Materials | | | |
|---|---|---|---|
| Chemical/Material Name | Abbreviation | CAS | Manufacturer |
| Dulbecco's phosphate buffered saline (contains 100 mg/L CaCl$_2$, 100 mg/L MgCl$_2$—6H$_2$O, 200 mg/L KCl, 200 mg/L KH$_2$PO$_4$, 8 g/L NaCl, 2.16 g/L Na$_2$HPO$_4$—7H$_2$O (DPBS) | DPBS | | Gibco (Life Technologies Limited), Paisley, UK |
| KNOX Original Unflavored Gelatine | Gelatin | | E.D. Smith Foods, Ltd, Ontario, Canada |
| WECOBEE M (solid at 25° C., room temperature) | | | Stepan Lipid Nutrition, Maywood, NJ |
| NEOBEE 1053 (liquid at 25° C., room temperature) | | | Stepan Lipid Nutrition, Maywood, NJ |
| A200 Fumed Silica | | | Evonik Industry, Parsippany, NJ |
| Xylitol | | | Now Foods, Bloomingdale, IL |

Methods

Method of Making Lozenges: The oil was heated to 80° C., mixed with fumed silica, and placed into a container compatible with the speed mixer. Sugar alcohol (e.g., xylitol) and other optional ingredients were dissolved in the DPBS by heating (80° C.) and stirred and then added to the container. The wt % in the tables for the CaCl$_2$, MgCl$_2$-6H$_2$O, KCl, KH$_2$PO$_4$, NaCl, Na$_2$HPO$_4$-7H$_2$O, and H$_2$O are presented calculated based on the known amount of DPBS buffer added and the amounts of the components therein. The solution was cooled to about 40° C. and placed in the speed mixer (FlackTek, Inc. DAC150.1 FVZ; Landrum, S.C.) for 30 seconds to 1 minute at 3500 rpm. The mixed solution was then transferred to a silicone mold or observed in its original speed mixer container and set at room temperature. The mixed solution was then re-heated to 45° C. for 5-10 minutes and then returned to room temperature to observe if separation occurred. No significant weight loss was observed with these lozenge samples due to low initial water weight.

Examples 1-3 and Comparative Examples C1 and C2

Example lozenges 1, 2 and 3 as well as comparative Examples C1 and C2 were made according to Table 2 below.

TABLE 2

| (all amounts are shown in wt-%) | | | | | |
|---|---|---|---|---|---|
| | Ex. 1 | Ex. 2 | Ex. 3 | Comp. Ex. 1 | Comp. Ex. 2 |
| Water Phase | | | | | |
| CaCl$_2$ | 0.00085 | 0.0003 | 0.0003 | 0.0003 | 0.0003 |
| MgCl$_2$—6H$_2$O | 0.00085 | 0.0003 | 0.0003 | 0.0003 | 0.0003 |
| KCl | 0.0017 | 0.0006 | 0.0006 | 0.0006 | 0.0006 |
| KH$_2$PO$_4$ | 0.0017 | 0.0006 | 0.0006 | 0.0006 | 0.0006 |
| NaCl | 0.068 | 0.024 | 0.024 | 0.024 | 0.024 |
| Na$_2$HPO$_4$—7H$_2$O | 0.018 | 0.0064 | 0.0064 | 0.0064 | 0.0064 |
| H$_2$O | 8.4 | 3.0 | 3.0 | 3.0 | 3.0 |
| Xylitol | 6.9 | 12 | 12 | 12 | 12 |
| Gelatin | 1.4 | 0 | 0 | 0 | 0 |
| Oil Phase | | | | | |
| WECOBEE M | 75.8 | 77.35 | 85.0 | 0 | 0 |
| NEOBEE 1053 | 0 | 0 | 0 | 77.4 | 85.0 |
| Fumed Silica | 7.5 | 7.7 | 0 | 7.7 | 0 |
| Homogenous after speed mixing? | Yes | Yes | Yes | Yes | No |
| Solid set upon cooling to room temperature? | Yes | Yes | Yes | No | No |
| Homogenous after re-heating to 80° C.? | Yes | Yes | No | Yes | No |

FIG. 1 shows photographs of the lozenges prepared above. The top row shows Example 3 and Comparative Examples 1 and 2. The bottom row shows Examples 2 and 3 that were poured after re-heating the mixed solution to 80° C. The lozenge of Example 2 remained homogeneous but Comparative Example 1 had visible separation of xylitol in the middle of the lozenge even after re-heating and pouring.

Examples 4-8 and Comparative Examples 3-7

Example lozenges 4-8 as well as Comparative Examples 3-7 were made according to Table 3 and Table 4 below.

TABLE 3

(all amounts presented in wt-% based on the total weight of the article)

|  | Ex. 4 | Ex. 5 | Ex. 6 | Ex. 7 | Ex. 8 |
|---|---|---|---|---|---|
| Water Phase |  |  |  |  |  |
| $CaCl_2$ | 0.00070 | 0.00047 | 0.00023 | 0.00012 | 0.00047 |
| KCl | 0.0014 | 0.00094 | 0.00046 | 0.00024 | 0.00094 |
| $KH_2PO_4$ | 0.0014 | 0.00094 | 0.00046 | 0.00024 | 0.00094 |
| NaCl | 0.056 | 0.38 | 0.018 | 0.0096 | 0.038 |
| $Na_2HPO_4$—$7H_2O$ | 0.015 | 0.010 | 0.0050 | 0.0026 | 0.010 |
| $H_2O$ | 6.9 | 4.6 | 2.3 | 1.2 | 4.6 |
| Xylitol | 8.0 | 5.3 | 2.7 | 1.3 | 5.3 |
| Oil Phase |  |  |  |  |  |
| WECOBEE M | 80 | 85 | 90 | 92 | 87 |
| Fumed Silica | 5.0 | 5.0 | 5.0 | 5.0 | 2.7 |
| Homogenous after speed mixing? | Yes | Yes | Yes | Yes | Yes |
| Homogenous after re-heating to 45° C. and then cooling? | Yes | Yes | Yes | Yes | Yes |

TABLE 4

(all amounts presented in wt-% based on the total weight of the article)

|  | Comp. Ex. 3 | Comp. Ex. 4 | Comp. Ex. 5 | Comp. Ex. 6 | Comp. Ex. 7 |
|---|---|---|---|---|---|
| Water Phase |  |  |  |  |  |
| $CaCl_2$ | 0.0011 | 0.00033 | 0.00011 | 0.00070 | 0.00023 |
| KCl | 0.0022 | 0.00066 | 0.00022 | 0.0014 | 0.00046 |
| $KH_2PO_4$ | 0.0022 | 0.00066 | 0.00022 | 0.0014 | 0.00046 |
| NaCl | 0.089 | 0.026 | 0.0089 | 0.056 | 0.018 |
| $Na_2HPO_4$—$7H_2O$ | 0.024 | 0.0071 | 0.0024 | 0.015 | 0.0050 |
| $H_2O$ | 11 | 3.3 | 1.1 | 6.9 | 2.3 |
| Xylitol | 39 | 12 | 3.9 | 8.0 | 2.7 |
| Oil Phase |  |  |  |  |  |
| WECOBEE M | 50 | 85 | 95 | 80 | 95 |
| Fumed Silica | 0 | 0 | 0 | 0 | 0 |
| Homogenous after speed mixing? | No | Yes | Yes | Yes | Yes |
| Homogenous after re-heating to 45° C. and then cooling? | No | No | No | No | No |

Upon flipping over the containers that had undergone a re-heating (45° C.) and cooling (room temperature) cycle after speed mixing, it was discovered that the samples without fumed silica (Comparative examples 3-7) had undergone separation and the water phase was trapped in the bottom of the container. When the samples were removed from the containers, there was visible water phase in Comparative examples 3-7, but not in Examples 4-8.

Illustrative embodiments include but are not limited to the following:

Articles comprising: from 70 wt-% to 99 wt-% of one or more plant based oil that is solid at 25° C. (room temperature), the weight percent based on the total weight of the article; and from 0.5 wt-% to 10 wt-% of fumed silica, the weight percent based on the total weight of the article, wherein the article is solid set and homogeneous.

Articles according to any of the above embodiments, wherein the one or more oil that is solid at room temperature is selected from hydrogenated vegetable oil.

Articles according to any of the above embodiments, wherein the one or more oil that is solid at room temperature is present in an amount from 75 wt-% to 99 wt-% based on the total weight of the article.

Articles according to any of the above embodiments, wherein the one or more plant based oils are present in an amount from 80 wt-% to 85 wt-% based on the total weight of the article.

Articles according to any of the above embodiments, wherein the fumed silica is present in an amount from 1 wt-% to 9 wt-% based on the total weight of the article.

Articles according to any of the above embodiments, wherein the fumed silica is present in an amount from 2 wt-% to 8.5 wt-% based on the total weight of the article.

Articles according to any of the above embodiments, wherein the fumed silica is present in an amount from 4 wt-% to 8.5 wt-% based on the total weight of the article.

Articles according to any of the above embodiments further comprising water in an amount from 0.5 wt-% to 10 wt-% based on the total weight of the article.

Articles according to any of the above embodiments further comprising water in an amount from 1 wt-% to 8 wt-% based on the total weight of the article.

Articles according to any of the above embodiments further comprising water in an amount from 2 wt-% to 5 wt-% based on the total weight of the article.

Articles according to any of the above embodiments further comprising sweeteners, mineral salts, buffering components, flavorants, preservative agents, humectants, or combinations thereof.

Articles according to any of the above embodiments further comprising aloe vera, folic acid, hyaluronic acid, ceramides, glycine, arginine, betaines or oxygenated glycerol triesters, vitamin E, vitamin B12, EDTA, cetyl pyridinium chloride, chlorhexidine, other antiseptics, or combinations thereof.

Articles according to any of the above embodiments, wherein the article comprises from 1 wt-% to 20 wt-% sweeteners based on the total weight of the article.

Articles according to any of the above embodiments, wherein the article is solid set.

Articles according to any of the above embodiments, wherein the article is homogeneous.

Articles according to any of the above embodiments, wherein the article is solid set and homogenous after being subjected to heating to 45° C., then speed mixing at 3500 RPM, and then cooling to 25° C.

Articles according to any of the above embodiments, wherein the article is solid set and homogenous after being subjected to heating to 80° C.

Articles according to any of the above embodiments, wherein the article can prevent, inhibit, disrupt, or any combination thereof the formation or maintenance of a biofilm in an area contacted with the article.

Articles according to any of the above embodiments, wherein the article can affect hydration loss in an area contacted by the article.

Articles according to any of the above embodiments, wherein the article can affect lubricity or lubriciousness of an area contacted by the article.

Methods of preventing, inhibiting, disrupting, or any combination thereof the formation or maintenance of a biofilm in an oral tissue, the method comprising: contacting an oral tissue with any of the above embodied articles.

Methods of affecting hydration loss in an oral tissue, the method comprising: contacting an oral tissue with any of the above embodied articles.

Methods of affecting lubricity or lubriciousness in an oral tissue, the method comprising:
contacting an oral tissue with any of the above embodied articles.

Methods of affecting the effects of xerostomia, dry mouth, or both, the method comprising: contacting an oral tissue with an article according to any of the above embodied articles.

Thus embodiments of oral compositions and methods of use are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. An article comprising:
   an oil phase comprising:
      one or more plant-based oil present in an amount from 75 wt-% to 99 wt-%;
      fumed silica present in an amount from 0.5 wt-% to 10 wt-%; and
   an aqueous phase comprising:
      water,
   wherein the one or more plant-based oil is a solid at 25° C.,
   wherein the article is solid set and homogenous at 25° C. without requiring emulsifiers,
   wherein the article is characterized by a homogeneity that is stable upon heating to 45° C. and subsequently cooling to 25° C., and
   wherein each wt-% is with respect to the weight of the article.

2. The article according to claim 1, wherein the one or more plant-based oil is a hydrogenated vegetable oil.

3. The article according to claim 1, wherein the one or more plant-based oil is present in an amount from 75 wt-% to 85 wt-% with respect to the weight of the article.

4. The article according to claim 1, wherein the fumed silica is present in an amount from 4 wt-% to 8.5 wt-% with respect to the weight of the article.

5. The article according to claim 1, wherein the water is present in an amount from 0.5 wt-% to 10 wt-% with respect to the weight of the article.

6. The article according to claim 1, further comprising sweeteners, mineral salts, buffering components, flavorants, preservative agents, humectants, or a combination thereof.

7. The article according to claim 1, further comprising aloe vera, folic acid, hyaluronic acid, ceramides, glycine, arginine, betaines, oxygenated glycerol triesters, vitamin E, vitamin B12, EDTA, cetyl pyridinium chloride, chlorhexidine, antiseptics, or a combination thereof.

8. The article according to claim 1, wherein the article is characterized by a homogeneity that is stable upon heating to 80° C. and subsequently cooling to 25° C.

9. The article according to claim 1, wherein the article prevents, inhibits, and/or disrupts the formation or maintenance of a biofilm in an area contacted with the article.

10. The article according to claim 1, wherein the article reduces hydration loss in an area contacted by the article.

11. The article according to claim 1, wherein the article increases lubricity or lubriciousness of an area contacted by the article.

12. A method of one or more of preventing, inhibiting, and disrupting the formation or maintenance of a biofilm in an oral tissue, the method comprising:
   contacting an oral tissue with an article according to claim 1.

13. A method of reducing hydration loss in an oral tissue, the method comprising:
   contacting an oral tissue with an article according to claim 1.

14. A method of increasing lubricity or lubriciousness in an oral tissue, the method comprising:

contacting an oral tissue with an article according to claim 1.

15. A method of reducing the effects of xerostomia, dry mouth, or both, the method comprising:

contacting an oral tissue with an article according to claim 1.

16. The article of claim 1, further comprising a sweetener and one or more mineral salt.

17. The article of claim 1, further comprising xylitol.

18. The article of claim 1, further comprising a calcium salt, a magnesium salt, a phosphate salt, or a combination thereof.

19. The article of claim 1, further comprising xylitol and one or more of a calcium salt, a magnesium salt, and a phosphate salt.

* * * * *